United States Patent [19]

Blum et al.

[11] Patent Number: 4,952,715

[45] Date of Patent: Aug. 28, 1990

[54] POLYSILAZANES AND RELATED COMPOSITIONS, PROCESSES AND USES

[75] Inventors: Yigal D. Blum, Menlo Park, Calif.; Edward J. Crawford, Danbury, Conn.

[73] Assignee: SRI International, Menlo Park, Calif.

[21] Appl. No.: 176,824

[22] Filed: Apr. 4, 1988

Related U.S. Application Data

[63] Continuation-in-part of Ser. No. 12,871, Dec. 1, 1986, which is a continuation-in-part of Ser. No. 908,685, Mar. 4, 1986, Pat. No. 4,788,300, which is a continuation-in-part of Ser. No. 727,415, Apr. 26, 1985, Pat. No. 4,612,383.

[51] Int. Cl.$^5$ ............................................. C07F 7/10
[52] U.S. Cl. ..................................... 556/409; 528/15; 528/28
[58] Field of Search ............................ 556/409, 15

[56] References Cited

U.S. PATENT DOCUMENTS

| | | | |
|---|---|---|---|
| 2,579,418 | 12/1951 | Cheronie | 556/409 X |
| 3,140,288 | 7/1964 | Peake | 260/288 |
| 3,228,895 | 1/1966 | Burke et al. | 556/409 X |
| 3,230,242 | 1/1966 | Firle | 556/409 |
| 3,291,760 | 12/1966 | Bayer | 556/409 X |
| 3,481,964 | 12/1969 | Imail et al. | 556/409 X |
| 3,655,615 | 4/1972 | Bush et al. | 556/409 X |
| 4,482,669 | 11/1984 | Seyferth et al. | 524/442 |
| 4,595,775 | 6/1986 | Arkles | 556/409 |
| 4,612,383 | 9/1986 | Laine et al. | 556/412 |
| 4,659,850 | 4/1987 | Arai et al. | 556/409 |
| 4,788,309 | 11/1988 | Laine et al. | 556/412 |

FOREIGN PATENT DOCUMENTS

| | | | |
|---|---|---|---|
| 8606377 | 11/1986 | PCT Int'l Appl. | 556/409 |
| 8705298 | 9/1987 | PCT Int'l Appl. | 556/409 |

OTHER PUBLICATIONS

Blum et al., *Organometallics*, 5:2081-2086 (1986).
Kruger et al., *J. Polymer Sci.*, 2A:3179-3189 (1964).
Zoeckler et al., *J. Org. Chem.*, 48:2539-2543 (1983).

*Primary Examiner*—Paul F. Shaver
*Attorney, Agent, or Firm*—Irell & Manella

[57] ABSTRACT

Silazanes and related compounds are prepared by providing a precursor containing one or more cyclic silazane units, causing polymerization to occur in the presence of a transition metal catalyst to form a polysilazane product. Further products may result from additional reaction. The novel compounds may be pyrolyzed to yield ceramic materials such as silicon nitride, silicon carbide and mixtures thereof. In a preferred embodiment, substantially pure silicon nitride and articles prepared therefrom are provided. Fibers, coatings, binders and the like may be prepared from the novel materials.

20 Claims, 1 Drawing Sheet

POLYSILAZANES AND RELATED COMPOSITIONS, PROCESSES AND USES

ORIGIN OF THE INVENTION

This invention was made with U. S. government support under the Office of Naval Research, Contract No. N00014-85-C-0668. The U. S. Government has certain rights in this invention.

CROSS-REFERENCE TO RELATED APPLICATIONS

This application is a continuation in part of U.S. application Ser. No. 012,874, filed Dec. 1, 1986, which is a continuation-in-part of U.S. application Ser. No. 908,685, filed Mar. 4, 1986, now U.S. Pat. No. 4,788,309 which is a continuation-in-part of U.S. application Ser. No. 727,415, filed Apr. 26, 1985 and now issued as U.S. Pat. No. 4,612,383.

DESCRIPTION

1. Technical Field

The invention relates to the synthesis of silazane compounds, i.e., compounds containing the structure Si-N in the molecule, and primarily concerns silazanes and polysilazanes which have one or more cyclomeric silazane units in their structure. The invention also relates (1) to the pyrolysis of these compounds after fabrication to give ceramic coatings, fibers and articles as well as (2) to the use of these compounds as binders.

2. Background

Polysilazanes and their derivatives are useful among other things, for the preparation of silicon nitride ($Si_3N_4$), silicon carbide (SiC), $Si_3N_4$/SiC alloys, $Si_3N_4$/carbon alloys, $Si_3N_4$/boron nitride alloys, and mixtures thereof. These ceramic materials can be used as structural materials, protective coatings, and electronic materials because of their hardness, strength, structural stability under extreme environmental conditions and their wide variety of electronic properties. In particular, these materials can be formed into ceramic fibers of value for reinforcement of composite materials. See, for example, (a) Department of Defense Proceedings, Fourth Metal Matrix Composites Technical Conference, May 19-21, 1981, prepared for DOD Metal Matrix Composites Information Analysis Center; and (b) J. J. Brennan, "Program to Study SiC Fiber-Reinforced Matrix Composites", Annual Report to Dept. of Navy (Nov. 1980), Contract No. N00014-78-C-0503.

Historically, polysilazanes were first synthesized by Stock et al almost 60 years ago (see, e.g., Stock, A. and K. Somieski, Ber. Dtsch. Chem. Ges. 54:740 (1921)) via a simple ammonolysis technique (Scheme I). However, this Scheme I

[Me$_2$SiNH]$_y$ + NH$_4$Cl approach usually produces mixtures of cyclomers where x is 3 to 5 that are obtained as the major products and small amounts of linear oligomers where y is less than or equal to about 10. Because of their low molecular weight, however, these linear oligosilazanes are too volatile to be used as preceramic materials.

In order to obtain higher molecular weight, nonvolatile materials, it was necessary to promote crosslinking reactions. In this manner, moderate molecular weight polysilazanes have been synthesized using a variety of techniques. See. e.g., Kruger, C. R. and E. G. Rochow, J. Polymer Sci. 2A:3179-3189 (1964). Rochow et al. discovered that ammonium chloride catalyzes crosslinking in simple oligodimethylsilazanes to form polysilazanes (Scheme II) which Scheme II

$\overline{M}_n$ = 10,000 D were proposed to contain cyclic monomer units crosslinked through nitrogen as suggested by the structure The Penn et al. work follows up on U.S. Pat. Nos. 3,853,567 to Verbeek and 3,892,583 to Winter et al., wherein a high temperature elimination/condensation reaction was shown to lead to soluble, highly crosslinked polymers as shown in Scheme III. Pyrolysis at high temperatures provides ceramic Scheme III $\overline{M}_w$ = 4200 D yields of 60% with a mixture of $Si_3N_4$ and SiC ceramic materials.

A related crosslinking approach described, inter alia, in U.S. Pat. Nos. 4,312,970, 4,340,619, 4,535,007 and 4,543,344 begins with the preparation of tractable polysilazanes having Me$_3$Si groups in the polymer backbone (Scheme IV) with the highest molecular weights reported in the available literature, i.e., about Mw~15,000 D and Mz~39,000 D:

Scheme IV

$\overline{M}_w$ = 15,000 D $\overline{M}_z$ = 39,000 D

Ceramic yields obtained from pyrolysis of this polymer are on the order of 45-55% with compositions of 96% $Si_3N_4$, 2% carbon and 2% oxygen after curing.

U.S. Pat. No. 4,482,669 to Seyferth et al. discloses that it is possible to crosslink low molecular weight cyclic oligomers containing Si-H bonds adjacent to N-H bonds via the following reaction:

Scheme V $\overline{M}_n = 1800\text{--}2200 \text{ D}$

The NH bond is catalytically activated by the strong base in this reaction. This type of crosslinking generates two-dimensional polymers, the solubility of which is limited by their sheet-like character. Ceramic yields of these materials are often quite high, up to about 86%, and typically provides $Si_3N_4$, SiC and carbon in a mole ratio of 0.88:1.27:0.75. If the pyrolysis is carried out in an $NH_3$ atmosphere, then the only product is $Si_3N_4$ with the other products remaining as slight impurities.

Zoeckler and Laine in J. Org. Chem. (1983) 48:2539-2541 describe the catalytic activation of the Si-N bond and in particular the ring opening of octamethylcyclotetrasilazane and polymerization of the ring-opened intermediate. Chain termination is effected by introducing $[CH_3)_3Si]_2NH$ as a coreactant giving rise to polymers $(CH_3)_3Si(CH_3)_2]_n\text{-}NHSi(CH_3)_3$ where n may be 1 to 12 or more depending upon the ratio of the chain terminator to the cyclic silazane. The catalyst used was $Ru_3(CO)_{12}$. Other publications are as follows: W. Fink, Helv. Chem. Acta., 49:P1408 (1966); Belgian Patent No. 665774 (1965); Netherlands Patent No. 6,507,996 (1965); D. Y. Zhinkis et al., Rus. Chem. Rev., 49:2814 (1980); K. A. Andrianov et al., Dok Akad. Nauk. SSSR, 227:352 (1976); Dok Akad. Nauk. SSSR 223:347 (1975); L. H. Sommer et al., JACS 91:7061 (1969); L. H. Sommer, J. Org. Chem. 32:2470 (1967); L. H. Sommer et al., JACS 89:5797 (1967).

In general, control of the polysilazane molecular weight, structural composition and viscoelastic properties plays a considerable role in determining the tractability (solubility, meltability or malleability) of the polymer, the processability during fabrication of fibers, shaped articles, etc., the ceramic yield, and the selectivity for specific ceramic products. In particular, the tractability plays a major role in how useful the polymer is as a binder, or for forming shapes, coatings, spinning fibers and the like. The more crosslinked a polymer is, the less control one has of its viscoelastic properties. Thus, highly crosslinked, low molecular weight polymers that are rigid materials or gels are not particularly useful for spinning fibers or as binders because they lack the required flexibility, viscosity and tenacity. By contrast, high molecular weight, flexible polymers as provided by applicants are extremely important. Such polymers represent a significant advance in the art, as they provide the flexibility and tenacity necessary in the fiber-spinning process and enhance the overall tensile strength of the spun fibers. In addition, the viscosities and the softening and melting points of the novel polymers may play a key role in binder applications, and in injection-molding processes in particular.

The parent application hereto, U.S. application Ser. No. 012,874, filed Dec. 1, 1986, describes the preparation of such high molecular weight, substantially linear polysilazanes. The disclosure of that application is hereby incorporated by reference in its entirety, as that application describes in some detail various compounds, methods and uses relevant to the present invention but not explicitly addressed herein.

The present application is directed to a subset of the compositions and methods described and claimed in Serial No. 012,874. Specifically, the present application is directed to silazanes and polysilazanes that include at least one cyclomeric silazane unit in the molecular structure.

As discussed above, several routes to polymers containing the monomeric units -[MeSiHNH]- have been developed. Ammonolysis of $MeSiHCl_2$ generates the low molecular weight cyclomer 1-cyclomethylsilazane (CMS)

which, as a non-viscous liquid that gives ceramic yields on the order of 20 wt.%, is impractical as a ceramic precursor. Arai et al. (see U.S. Pat. No. 4,659,850) have demonstrated how a modification of the ammonolysis process results in a higher molecular weight species. The Arai et al. group reacted dichloromethylsilane with ammonia in the presence of pyridine at 80° C. The Lewis base complexes with the chlorosilane and causes the formation of a linear-cyclomer copolymer having trisilylated nitrogen bridges ($M_n=1100\text{-}1800$ D, ceramic yield about 44 wt %). Similarly, Matsumoto et al. (Japan Patent Publication [Kokai] No. 61-72607) disclose reaction of a dihalosilane with ammonia which is stated to give relatively high molecular weight, highly viscous polysilazanes.

The Seyferth et al. polymers (U.S. Pat. No. 4,482,669, cited supra) formed by dehydrocyclodimerizing CMS oligomers, are, as noted above, very rigid structures. This rigidity, although responsible in part for the high ceramic yields obtained upon pyrolysis, prevents the polymer from having softening or melting points. Such polymers with an $M_n$ over about 2500 D are brittle, intractable gels. No liquid polymers, even of low molecular weight, have been formed by this KH catalysis method.

The presently claimed compounds are believed to include the first reported polymers of $[MeSiHNH]_n$ that are either liquid or have a softening or melting point, indicating higher structural flexibility and perhaps higher linearity as well. Like the parent application hereto, the present disclosure demonstrates how transition metal catalysis may be used for modifying the characteristics of inorganic polymers and, specifically, how control over polymer properties, pyrolysis results and the final ceramic compositions can follow directly from the selection of the precursor, the chosen chemical method and the reaction conditions.

DISCLOSURE OF THE INVENTION

It is thus a primary object of the present invention to provide improved methods of preparing silazanes and, in particular, polysilazanes having one or more cyclomeric silazane units in their molecular structure.

It is another object of the invention to provide novel compounds which include such polysilazanes.

It is still another object of the invention to provide a method of making a ceramic composition including silicon nitride and/or silicon carbide, by pyrolyzing the polysilazane compounds provided herein.

It is a further object of the invention to provide a method of coating substrates with ceramic materials as described herein.

Other objects of the invention include methods of making fibers, fine or monodispersed powders, coatings, and the like, using the preceramic polymers and the ceramic materials disclosed herein.

Still other objects of the invention include methods of using the polymers of the invention as binders, as adhesives, in infiltration applications, and in matrix and composite materials.

Additional objects, advantages and novel features of the invention will be set forth in part in the description which follows, and in part will become apparent to those skilled in the art on examination of the following, or may be learned by practice of the invention.

In one aspect of the invention, a polysilazane is prepared having n recurring units given by structures (I) or (II) or both where m is 0 or an integer, n is an integer greater than 1, the R substituents may be the same or different and are selected from the group consisting of hydrogen, lower alkyl, lower alkenyl, silyl, aryl including phenyl or benzyl, and amino, unsubstituted or substituted with 1 or 2 lower alkyl or silyl groups, X is —NR'— or —NR'—Y—NR'— where Y is an optional linking group which, if present, is lower alkyl or silyl (including silazanyl), and R' and R" are independently selected from the group consisting of hydrogen, lower alkyl, lower alkenyl, silyl including silazanyl, and aryl including phenyl or benzyl. The polysilazane is prepared by pyrolyzing a silazane precursor in a selected environment in the presence of a transition metal catalyst, the precursor having the structure In other aspects of the invention, polysilazanes given by structures (I) or (II) are pyrolyzed to give ceramic products such as shaped articles, fibers, powders, and the like. The novel polymers in general display improved processability and thermolytic properties.

Modes for Carrying Out the Invention

A. Definitions

"Silazanes" as used herein are compounds which contain one or more silicon-nitrogen bonds. The term "polysilazane" is intended to include oligomeric and polymeric silazanes, i.e., compounds which include two or more monomeric or cyclomeric silazane units.

The number average molecular weight $M_n$ of a polymer distribution is given by $$M_n = \frac{\Sigma Wi}{\Sigma Ni},$$

wherein Wi is the weight of each individual polymeric or oligomeric species and Ni is the number of individual species in the distribution. Where not otherwise specified, molecular weights for a particular polymer distribution obtained directly will be given as calculated prior to any separation or isolation step.

The "ceramic yield" of a compound upon pyrolysis indicates the ratio of the weight of the ceramic product after pyrolysis to the weight of the compound before pyrolysis.

A "lower alkyl" or "lower alkenyl" group is an alkyl or alkenyl group, respectively, having 1-6 carbon atoms therein.

"Silyl" as used herein is an —$SiR_2$— or —$SiR_3$ moiety where R is hydrogen, lower alkyl, lower alkenyl or amino, unsubstituted or substituted with 1 or 2 lower alkyl or lower alkenyl groups. "Silyl" moieties thus include "silazanyl" groups.

The parent application hereto defines the two types of reactions by which silazanes and polysilazanes are formed according to the method of the invention. In the type (a) reaction, a precursor is initially provided which contains at least one Si-N bond. Cleavage of an Si-N bond in the precursor is catalytically effected in the presence of hydrogen or a hydrogen donor, and the cleavage product is then caused to react with a second cleavage product or with a compound containing an Si—H bond, an N—H bond, or both, to produce an initial silazane product having at least one newly formed Si—N bond.

In what applicants have referred to as the "type (b)" reaction, one or more reactants are provided which in combination contain an Si—H bond and an N—H bond, and reaction is caused to occur between the two bonds in the presence of a transition metal catalyst, whereby an initial silazane product is provided having at least two Si-N bonds, at least one of which is newly formed. The polymerization of cyclomer-containing precursors as described in the present application, as will be discussed, falls within that class of reactions designated as "type (b)".

B. The Precursor Material

As described in U.S. Ser. No. 012,874, the precursor material may be monomeric, oligomeric or polymeric. The precursor is a silazane having one or more units of the formula where m is 0 or an integer, and the R substituents, which may be the same or different, are selected from the group consisting of hydrogen, lower alkyl, lower alkenyl, silyl, aryl including phenyl or benzyl, and amino, unsubstituted or substituted with 1 or 2 lower alkyl groups. The precursor, in order to provide the desired "bridged" product, must have either: (1) an Si—H and an N—H bond (i.e., at least one R and at least one R" are hydrogen); or (2) 2 Si—H bonds (i.e., at least two R substituents are hydrogen). The precursor may be either a cyclic silazane as defined by the above structure alone, or it may be a chain or network of such cyclomers. In the latter case, the molecular weight of the precursor is preferably less than about 2000 D. Such a chain or network may include amine or silyl bridges between the cyclomers.

These precursors may be prepared by the method described in the parent application hereto, i.e., by reaction of a dihalogenated silane with ammonia or an amine. In a particularly preferred embodiment, the 1-cyclomethylsilazanes (CMS) given by the above structure are prepared by reaction of Me(H)SiCl$_2$ with ammonia, at low temperature (preferably 0° C. or lower) in a suitable solvent. The "R" substituents are introduced by appropriate selection of the dihalogenated silane, i.e., by using R$_2$SiCl$_2$ at the outset.

CMS is particularly suitable for dehydrocoupling catalysis by transition metals because of the multiple Si—H and N—H sites which enable bridging between the cyclomers. As will be addressed in some detail, the characteristics of the polymeric products obtained by transition metal-catalyzed dehydrocoupling are very different from those formed by dehydrocyclodimerization as described by Seyferth et al., supra. In an alternative embodiment of the invention, the doubly bridged polymers disclosed in U.S. Pat. No. 4,482,669 to Seyferth et al. are used as precursors in the method herein to give polysilazane structures having single as well as double bridges, i.e., given by the structure Such polymers are more flexible but nevertheless give high ceramic yields on the order of those obtained with the doubly bridged precursors.

The precursors described may also be modified prior to polymerization by inclusion of latent reactive groups such as hydrogen, amine, alkoxy, sulfide, alkenyl, alkynyl, etc., or crosslinked with suitable crosslinking reagents

C. Formation of Polysilazanes

Depending on the reactants and reaction conditions chosen, the above-described precursors are polymerized catalytically to give polysilazanes having n recurring units of either (I) or (II) or both where m is 0 or an integer, n is an integer greater than 1, the R substituents may be the same or different and are selected from the group consisting of hydrogen, lower alkyl, lower alkenyl, silyl, aryl including phenyl or benzyl, and amino, unsubstituted or substituted with 1 or 2 lower alkyl or silyl groups, X is —NR'— or —NR'—Y—NR' where Y is an optional linking group which, if present is lower alkyl or silyl (including silazanyl), and R' and R" are independently selected from the group consisting of hydrogen, lower alkyl, lower alkenyl, silyl including silazanyl, and aryl including phenyl or benzyl. Typically, "n" gives a molecular weight on the order of 500 to 10,000 D.

The polysilazanes so provided, depending on the reaction conditions chosen—i.e., on the presence and amount of ammonia or amine used, solvent and temperature -- may be substantially linear, somewhat bridged, or highly crosslinked, and may contain repeating units of only structure (I), only structure (II), or an admixture of both. For example, a higher nitrogen content may be effected by increasing the exposure of the precursor to ammonia, which, as illustrated by Scheme VI, will introduce more nitrogen "bridges" into the polymer between individual cyclomer units. A higher nitrogen content may also be achieved by increasing the exposure to a substituted amine, in which case, as illustrated by Scheme VII, nitrogen-containing substituents are introduced into the cyclomers (pendant to individual silicon atoms in the cyclomer rings) in addition to nitrogen bridging.

The optional amine co-reactant present in the polymerization environment, may be generally represented by the formula γNH$_2$, where γ is hydrogen, lower alkyl, silyl optionally substituted with one or more alkyl groups, or —(CH$_2$)$_x$NH$_2$ where x is an integer in the range of 0 and 20 inclusive.

In all cases, the reaction is carried out catalytically.

Catalysts suitable for carrying out polymerization of these precursors are any type of transition metal catalysts such as those indicated in Table 1, below, which are homogeneous catalysts that either dissolve in the reactants or in a solvent used to dissolve the reactants. Heterogeneous catalysts such as those of Table 2 may also be used or mixtures of homogeneous catalysts and/or heterogeneous catalysts. (It should be pointed out here that the "homogeneous" and "heterogeneous" classifications are made herein on the basis of solubility in organic solvents. However, it is not uncommon that during the reactions, homogeneous catalysts may be converted into a heterogeneous form and vice versa.) These catalysts may include any number of ligands, including carbonyl, amino, halo, silyl, hydrido, phosphine, arsine and organic ligands. Tables 1 and 2 illustrate a number of catalysts which may be used.

The catalyst(s) may be supported on a polymer, inorganic salt, carbon, or ceramic material or the like. The heterogeneous catalyst may be provided in a designed shape, such as particles, porous plates, etc.

The catalyst can be activated if desired such as by heating alone or by concurrent treatment of the reaction medium with particulate or nonparticulate radiation The catalyst may also be activated by promoters such as acids, bases, oxidants or hydrogen, or may be stabilized by reagents such as amines, phosphines, arsines and carbonyl. The concentration of catalyst will usually be less than or equal to about 5 mole % based on the total number of moles of reactants, usually between about 0.1 and 5 mole %. In some instances, however, catalyst concentration will be much lower, on the order of 20 to 200 ppm.

TABLE 1,

HOMOGENEOUS CATALYSTS $H_4Ru_4(CO)_{12}$, $Fe(CO)_5$, $Rh_6(CO)_{16}$, $Co_2(CO)_8$, $(Ph_3P)_2Rh(CO)H$, $H_2PtCl_6$, nickel cyclooctadiene, $Os_3(CO)_{12}$, $Ir_4(CO)_{12}$, $(Ph_3P)_2Ir(CO)H$, $NiCl_2$, $Ni(OAc)_2$, $Cp_2TiCl_2$, $(Ph_3P)_3RhCl$, $H_2Os_3(CO)_{10}$, $Pd(Ph_3P)_4$, $Fe_3(CO)_{12}$, $Ru_3(CO)_{12}$, transition metal hydrides, transition metal salts (e.g., $ZnCl_2$, $RuCl_3$, $NaHRu_3(CO)_{11}$) and derivatives, $PdCl_2$, $Pd(OAc)_2$, $(\phi CN)_2PdCl_2$, $[Et_3SiRu(CO)_4]_2$, $(Me_3Si)_2Ru(CO)_4$, $[Me_2SiXSiMe_2]Ru(CO)_4$, and mixtures, thereof.

TABLE 2

HETEROGENEOUS CATALYSTS

Pt/C, Pt/BaSO$_4$, Cr, Pd/C, Co/C, Pt black, Co black, Ru black, Ra-Ni, Pd black, Ir/Al$_2$O$_3$, Pt/SiO$_2$, Rh/TiO$_2$, Rh/La$_2$O$_3$, Pd/Ag alloy, LaNi$_5$, PtO$_2$, and mixtures thereof.

The reaction is carried out in solution with the solvent comprising either the reactants themselves or an added nonreactive organic solvent such as a hydrocarbon, an ether (e.g., ethyl ether, tetrahydrofuran), a halogenated hydrocarbon (CHCl$_3$, Ch$_2$Cl$_2$, ClCHF$_2$, ClCH$_2$CH$_2$Cl), an aromatic such as benzene, toluene, or methylphenyl ether, or a polar solvent such as THF, acetonitrile, pyridine, or a tertiary amine. Some reactions may, if desired, be carried out in the gas phase by flowing the reactant(s) over the transition metal catalyst.

Mild temperatures that will activate the catalyst are typically used. Such temperatures will normally be in the range of −78° C. to 250° C., as described in U.S. Ser. No. 012,874. In the particular reactions described and claimed herein, milder temperatures, on the order of room temperature or higher—i.e., about 0° C. to 150° C., more preferably about 20 C. to 90° C.

Reaction in ammonia will give the nitrogen-bridged structure represented by (I), while reaction in a substituted amine such as monomethylamine gives the structure represented by (II) in which the cyclomers are bound to each other directly, without a bridging atom.

The following schemes illustrate specific examples of the polymerization r(R)actions that give polysiloxanes containing structures (I) and/or (II):

Scheme VI

Scheme VII

Scheme VIII

The suggested structures obtained in the above schemes are based on a combination of $^1$H NMR, IR and elemental analysis. In contrast to the dehydrocyclodimerization (DHCD) reaction described in, inter alia. U.S. Pat. No. 4,482,699 to Seyferth et al., calculations carried out by applicants suggest that the loss of Si-H bonds is closer to one per "precursor" molecule rather than two for the DHCD reaction. Also, the polymer produced from the reaction of Scheme VIII, although very viscous, is still a liquid, despite the rather high molecular weight ($M_n$ about 2030 D).

The reaction with ammonia (Scheme VI) generates polymers that have softening or melting points. These melting points can be controlled by the reaction conditions and directly correspond to molecular weight. To applicants' knowledge, these are the first reported polymers with units of [MeSiHNH]$_n$ that do have a measurable melting point. Since the molecular weights are as high as those obtained by DHCD, the polymers' melting points indicate higher structural flexibility and perhaps higher linearity of the polymer. Because of its increased latent reactivity, the higher flexibility of the polysilazane obtained in Scheme VI does not cause a decrease in ceramic yields after pyrolysis (80 and 85% under $N_2$ and $NH_3$ respectively).

The polymerization of CMS in the presence of monomethylamine (Scheme VII) is slowed relative to the ammonia reactions and is similar to the polymerization without any additional amine (Scheme VI). However, a quantitative addition of monomethylamine to the polymer as pendant groups was observed and confirmed by $^1$H NMR and elemental analysis. These groups increase the viscosity of the product as well as the latent reactivity. This latent reactivity is observed in the faster gelation process when the solvent volume is reduced and the higher ceramic yields that are obtained relative to the product of reaction Scheme VI.

The polymer obtained in Scheme VIII may be further reacted to give a co-polymer of the structures obtained in Schemes VI and VII, i.e., with nitrogen bridges present linking some of the cyclomers and not present between others.

D. Pyrolysis to Ceramic Materials

Another important advantage of the compositions and methods of the present invention is the specificity and degree of ceramic yield upon pyrolysis. Generally, an increase in the polymer nitrogen content results in higher nitrogen content and lower carbon content in the ceramic product.

Silicon nitride may be provided with Si and N content higher than about 80 wt % upon pyrolysis of the polysilazanes provided herein when pyrolysis is conducted under nitrogen, argon or other inert atmosphere, or higher than about 95% upon pyrolysis of the polysilazanes in an ammonia or other amine atmosphere. Carbon-free polysilazanes which may be prepared according to the method herein may provide silicon nitride of even higher purity, i.e., 98-99% or higher.

Procedurally, pyrolysis, according to the preferred method of the present invention, is carried out as follows A polysilazane prepared as described above is heated in a preferably inert atmosphere such as in nitrogen or argon at a predetermined heating rate. If desired, pyrolysis may also be carried out in a reactive atmosphere, e.g., under $NH_3$, $H_2O_2$, $H_2O$, $N_2O$, an alkylamine, or the like. As demonstrated in Examples 31 and 32 of U.S. Ser. No. 012,874, the heating rate during pyrolysis is strongly correlated to the yield of ceramic material obtained preferred heating rates for bulk pyrolysis are between about 0.1° C. and 10° C. per minute, preferably between about 0.5° C. and 2° C. per minute, with a particularly effective heating rate, optimizing ceramic yield, of about 0.5° C. per minute In some applications, however, flash pyrolysis may be preferred (e.g., in coating applications). The temperature of the polymer is typically raised to between about 500° C. and about 900° C., optionally higher, to about 1600° C.-1800° C., to provide crystallization, sintering or grain growth of the ceramic material The heating process may include one or more isothermal holding steps, in order to control the pyrolysis, to provide more crosslinking at moderate temperature (less than about 400° C) and to further increase the yield of the final product. If desired, pyrolysis may be carried out in the presence of a catalyst; examples of suitable catalysts are set forth in Tables 1 and 2. These tables are intended for illustrative purposes only and are not intended to limit the catalysts which could be used herein to those recited.

Optionally, pyrolysis may be carried out only partially, i.e., in applications where it is not necessary to obtain a fully pyrolyzed material. Such applications include coatings, or silazane rubbers, glasses, etc., or where the environment of a material can be damaged by high temperatures Such "partial pyrolysis" or partial curing may be carried out at temperatures lower than 500° C.

Depending on the preceramic polymer pyrolyzed, then, the ceramic products may include silicon nitride, silicon carbide, and silicon nitride/silicon carbide alloys.

E. Ceramic Coating Procedures

The ceramic materials provided herein are useful in a number of applications, including as coatings for many different kinds of substrates.

Silicon nitride and silicon carbide coatings may be provided on a substrate, for example, by a variation of the pyrolysis method just described. A substrate selected such that it will withstand the high temperatures of pyrolysis (e.g. metal, glass, ceramic, fibers, graphite) is coated with a preceramic polymer material by dipping in a selected silazane polymer solution, or by painting, spraying, or the like, with such polymer solution, the solution having a predetermined concentration, preferably between about 0.1 and 100 wt. %, more preferably between about 5 and 10 wt % for most applications. The polymer is then pyrolyzed on the substrate by heating according to the pyrolysis procedure outlined above. In such a method, pyrolysis can be conducted relatively slowly, i.e., at a heating rate between about 0.1° C. and 2.0° C. per minute, in order to allow evolved gas to escape without forming bubbles in the coating, and can include one or more isothermal holding steps. In some instances, for example, with relatively temperature-sensistive materials, or where a rapid-coating process is desired, a flash pyrolysis step may be preferred. Repeated, multiple coatings may be applied where a thicker layer of material is desired, with partial curing or gradual or flash pyrolysis following each individual coating step.

The pyrolysis temperature will vary with the type of coating desired. Typically, temperatures will range from about 350° C. to about 1100° C. Lower temperatures, below about 500° C., can result in only partially pyrolyzed polymer.

Optionally, the liquid or dissolved polymer may be admixed with ceramic powders such as silicon nitride or silicon carbide optionally admixed with sintering aids such as aluminum oxide, silica, yttrium oxide, and the like, prior to coating. Crosslinking agents may be included in the coating mixture as well.

The above coating procedure is a substantial improvement over the conventional, chemical vapor deposition (CVD) method of producing silicon nitride coatings in which the appropriate compounds (e.g., $SiH_4$ and $NH_3$ or volatile silazane) react in the vapor phase to form the ceramic which deposits on the target substrate. CVD is typically an inefficient, time-consuming process which requires costly and specialized equipment. The procedure described above for producing coatings containing silicon nitride can be done with a conventional furnace. Further, the method leads to heat-stable, wear-, erosion-, abrasion, and corrosion-resistant silicon nitride ceramic coatings. Because silicon nitride is an extremely hard, durable material, many applications of the coating process are possible. One specific application is in gas turbine engines, on parts which are particularly susceptible to wear. Also, because silicon nitride is an insulator, the coating process could be used as the dielectric material of capacitors, or for providing insulating coatings in the electronics industry. Other applications are clearly possible.

In an alternative embodiment of the invention, a substrate is spray-coated with ceramic or preceramic materials. Such a procedure provides for a higher density coating, as well as for a greater degree of homogeneity. Preceramic coatings may be provided on a substrate, or at higher temperatures, one or more ceramic coatings may be provided. Gaseous species, such as silane and ammonia, which are capable of reacting to form preceramic polymers, are introduced into a nozzle. The gases are admixed within the nozzle and passed over a transition metal catalyst bed contained within the nozzle, suitable transition metal catalysts herein are selected from those set forth in Table I and II. The catalyst bed initiates the formation of preceramic materials from the gaseous species. At the nozzle, the gaseous preceramic materials are mixed with inert or reactive gases introduced into the apparatus through one or more inlets, and the substrate surface is coated with a mixture of these materials. Such a procedure, which provides a suspension of liquid preceramic materials in air, may be used for the preparation of fine powders, as well.

The desired polymerization reaction designated as type (a) or type (b) thus takes place as the gases are passed over the catalyst bed. The inert gas delivers the preceramic materials to the substrate surface, or, if the gas phase is heated, it can deliver actual ceramic powders or mixtures of powders and preceramic polymer having controlled-size particles. The process can be used to form ultrafine aerosols of precursors and homogeneous catalyst solutions for ultrafine particle applications.

F. Fabrication of Molded Ceramic Bodies

The preceramic polymers are provided herein, admixed with ceramic powders, may be used to form three-dimensional articles by injection- or compression-molding using procedures substantially as described in co-pending application Ser. No. 012,874. The results as demonstrated in the examples of that application indicate that the procedure may also be successful in the absence of sintering agents.

G. Preparation of Fibers

The polymers provided in the present invention can be used for preceramic fiber spinning.

Three general spinning techniques are commonly used: (a) melt spinning, in which the polymer is spun from its melt and solidified by cooling; (b) dry spinning, in which the polymer is at least partially dissolved in solution and pulled out through the spinneret into a heat chamber, then solidified by solvent evaporation; and (c) wet spinning, in which a concentrated polymer solution is spun into a coagulation or regeneration bath containing another solvent in which the polymer is not soluble. In addition, gel-type polymers can be spun from very viscous solutions. These tractable polymers rapidly gel and crosslink upon removal of solvent after spinning due to high latent reactivity. Polymeric fibers so formed are intractable.

Additional, relatively small quantities (0.1–5.0 wt. %) of a very high molecular weight substantially linear organic polymer (100,000–5,000,000D) may be mixed with the inorganic polymer to support and improve the fiber strength after spinning, as taught in, e.g., U.S. Pat. Nos. 3,853,567 to Verbeek and 3,892,583 to Winter et al.

The supporting technique is especially useful when low molecular weight and/or nonlinear polymers having a very low degree of chain entanglement are used.

One problem encountered in ceramic fiber fabrication derives from the fusability of inorganic polymers during pyrolysis. This fusability results in structural problems in the spun fiber. Polymers produced by the present invention, however, overcome the fusability problem, providing that the catalytic process as described herein is actually incorporated into the fiber-spinning process. For example, a high molecular weight polysilazane may be mixed with homogeneous catalyst and heated in spinneret or in the curing chamber to cause reactions of type (a) or (b) or both to occur and increase the degree of crosslinking in the fiber. Alternatively, the spinneret can itself be a catalytic bed. Crosslinking agents may also be included in the fiber-spinning process to provide additional crosslinking; similarly, latent reactive groups (e.g., free amino moieties) may be present, as well, for the same reason, even in the absence of catalyst Alternatively, the spun fiber can be exposed to an ammonia environment and cured at a temperature below the melting point.

H. Other Applications

Many other applications of the novel polymers of the invention are clearly possible The results summarized in part F, for example, suggest combination of polysilazanes and related compounds with other ceramic powders (e.g., SiC, BN, $B_4C$) to produce composite articles. Such a composite of, e.g., a silazane polymer/SiC powder mixture may give an article having improved oxidation resistance. Another application would be to use the novel polymers in dissolved or liquid form as binders combined with ceramic powders so as to provide a fluid polymer/powder solution.

Infiltration and impregnation processes are additional possibilities, as discussed, for example, in U.S. Pat. No. 4,177,230 to Mazdiyasni et al and in W. S. Coblenz et al in *Emergent Process Methods for High-Technology Ceramics*, ed. Davis et al (Plenum Publishing, 1984). Two general methods are typically used. One is a high-vacuum technique in which a porous ceramic body is placed in a liquid or slightly dissolved preceramic polymer solution After a high vacuum infiltration, the article is pyrolyzed to achieve a higher density. The second method is high-pressure infiltration. Either of these methods can be adapted for the polymers of the invention. Either of these methods can be adapted for the polymers of the invention. In addition, low molecular weight oligosilazane solutions having higher mobility in the porous ceramic body can be incubated with the ceramic body and a transition metal catalyst, followed by incubation of the oligomeric reactants and reaction of type (a) or (b) or both. In situ chain extension or crosslinking will reduce the mobility and volatility of the oligomeric starting materials.

Other applications of the novel polymers include use as a cement to "bond" ceramic materials such as powders, ceramic fibers, and three-dimensional forms. Bonding of fibers followed by pyrolysis can yield matrices or matrix composites. In some application, ceramic articles may be joined by the polymers, under pressure, followed by pyrolysis. The chemical interactions discussed in part F between the polymer and ceramic powders may occur in bonding to enhance the strength of the cement.

It is to be understood that while the invention has been described in conjunction with the preferred specific embodiments thereof, that the foregoing description as well as the examples which follow are intended to illustrate and not limit the scope of the invention, which is defined by the scope of the appended claims. Other aspects, advantages and modifications within the scope of the invention will be apparent to those skilled in the art to which the invention pertains.

EXAMPLES

Experimental: Unless otherwise indicated, the reagents used were obtained from the following sources silanes, from Petrarch Systems, Inc., Bristol, Pa.; organic reagents including amines, from Aldrich Chemical Co, Milwaukee, Wis.; gases, from Matheson, Seacaucus, N.J.; and catalysts, from Strem, Newburyport, Mass.

EXAMPLE 1

Preparation of Cyclomethylsilazane (CMS) ($-78°$ C.): A 2 liter 3-neck flask fitted with an overhead stirrer, nitrogen inlet, and a rubber septum was well flushed with nitrogen. 500 ml anhydrous ether (from a freshly opened can) were added followed by 156.0 ml (172.5 g, 1.5 moles) Me(H)SiCl$_2$. The solution was cooled to $-78°$ C. with a dry ice acetone bath. Ammonia, dried by passing through KOH, was bubbled through the reaction for 4 hours. A large amount of white precipitate was formed The reaction was allowed to come to room temperature with the NH$_3$ purge over two more hours then filtered in a dry box. The white precipitate was extracted with 3×350 ml boiling THF, filtered, and the combined filtrates were reduced to approx. 300 ml. NH$_3$ was bubbled through this filtrate for 30 minutes at room temperature to ensure complete reaction. The cloudy mixture was re-filtered through a sintered glass filter to remove the additional white solid. A very pale yellow liquid (70.3 g, 79%) remained after solvent removal. The GC-MS of this liquid showed the major volatile species to be cyclomers of the structure —[CH$_3$Si(H)NH]—$_n$ and cyclomers with side groups. There is some evidence of rearrangement reactions on the silicon atoms during the process. The M$_n$ was 720 d. The $^1$H NMR of the oligomer shows a ratio of SiH: NH: SiCH$_3$ (0.9: 0.6: 3.0). Elemental Analysis: %C 23.29, %H 8 48, %N 23.18, %Si 38.08, %Cl <0.1. Theoretical for [—CH$_3$Si(H)NH—]: %C 20.34, %H 8.47, %N 23.73, %Si 47.46. This compound gave a ceramic yield of 35 wt % after pyrolysis under nitrogen to 850° C.

EXAMPLE 2

Preparation of Cyclomethylsilazane (CMS) (0° C.): A 3-neck, 1000 ml flask fitted with an overhead stirrer and rubber septa was well flushed with nitrogen. 500 ml anhydrous ether (from a freshly opened can) were added followed by 250 ml (276 g, 2.40 moles) Me(H)SiCl$_2$. Ammonia, dried by passing through KOH, was bubbled through the reaction at 0° C. for 4 hours then at room temperature for 4 hours. A large amount of white precipitate formed. The reaction was then stirred under nitrogen at room temperature for 2 hours. One half of the reaction was filtered in the dry box. When NH$_3$ was bubbled through this filtrate, more precipitate formed, indicating that the reaction was incomplete. The NH$_3$ was bubbled for several more hours at room temperature until no more precipitation was apparent. The reaction was re-filtered to remove the additional white solid. All the white precipitate was extracted with 3×300 ml boiling THF, filtered, and the combined filtrates were reduced under vacuum to give a very pale yellow liquid (44.5 g). The GC-MS of this liquid showed the major volatile species to be cyclotetramers with a m/e of 236. The M$_n$ was 1134 D (some drift). $^1$H NMR (CDCl$_3$): 4.82, 4.62, 4.37 (m, 0.92 H, SiH), 0.85 (m, 0.84 H, NH), 0.16 (bs, 3.0 H, SiCH$_3$). Elemental Analysis: %C 20.82, %H 8.39, %N 22.02, %Si 42.17, %Cl <0.1. Theoretical for [—(CH$_3$)Si(H)NH—]: %C 20.34, %H 8.47, %N 23.73, %Si 47.46.

EXAMPLE 3

Preparation of Cyclomethylsilazane (CMS) (0° C.): A 3-neck, 1000 ml flask fitted with an overhead stirrer and rubber septa was well flushed with nitrogen. 450 ml anhydrous ether (from a freshly opened can) were added followed by 50 ml (55.25 g, 0.480 moles) Me(H)SiCl$_2$. Ammonia, dried by passing through KOH, was bubbled through the reaction at 0° C. for 2 hours. A large amount of white precipitate formed The reaction was then stirred under nitrogen at room temperature for 12 hours then filtered in the dry box. All the white precipitate was extracted with 5×80 ml dry ether, filtered, and the combined filtrates were reduced under vacuum to give a colorless liquid. The M$_n$ was 633 D. $^1$H NMR (CDCl$_3$): 4.82, 4.64, 4.39 (m, 0.74 H, SiH), 0.80 (m, 0.74 H, NH), 0.18 (bs, 3.0 H, SiCH$_3$).

EXAMPLE 4

Preparation of Cyclomethylsilazane (CMS) ($-78°$ C.): A 1 liter, 3-neck flask fitted with an overhead stirrer, nitrogen inlet, and a rubber septum was well flushed with nitrogen. 300 ml anhydrous ether (from a freshly opened can) were added followed by 30.0 ml (33.15 g, 0.288 moles) Me(H)SiCl$_2$. The solution was cooled to $-78°$ C. with a dry ice acetone bath. Ammonia, dried by passing through KOH, was bubbled through the reaction for 4 hours. A large amount of white precipitate formed. The reaction was allowed to come to room temperature with the NH$_3$ purge over 3 hours then stirred under nitrogen for 14 hours. A white precipitate was collected by filtration then extracted with 3×150 ml boiling THF. The combined filtrates were reduced to a colorless liquid. The M$_n$ was 780 D.

EXAMPLE 5

Polymerization of CMS with Ru$_3$(CO)$_{12}$ (No solvent): 3.0 g CMS (from Example 1) and 6.0 mg (0.00936 mmoles) Ru$_3$(CO)$_{12}$ were added under nitrogen to a quartz reactor. The mixture was heated at 60° C. with magnetic stirring. During the reaction, the pressure was released approx. every 2.5 hours. Solvent was removed from the pale, yellow-orange solution under vacuum after 11 hours to give a very viscous oil. The $^1$H NMR indicated that the polymer had a ratio of 0.71 H: 0.56 H: 3H for SiH: NH: SiCH$_3$. Elemental Analysis: %C 22.26, %H 7.62, %N 22.75, %Si 37.72. The polycyclomethylsilazane (PCMS) produced a 72 wt % ceramic yield after pyrolysis under nitrogen and 77 wt % under $NH_3$. Elemental Analysis (after pyrolysis): %C 16.27, %H 0.84, %N 25.54, %Si 51.80.

EXAMPLE 6

Polymerization of CMS with $Ru_3(CO)_{12}$ (THF): 5.0 g CMS (from Example 2), 10.0 mg (0.0156 mmoles) $Ru_3(CO)_{12}$, and 5.0 g THF were placed in a stainless steel pressure reactor under nitrogen. The reaction was heated at 60° C. with magnetic stirring. During the reaction, the pressure increased 180 psi. The pressure was released after 10 hours and solvent was removed from the pale, yellow-orange solution under vacuum to give a moderately viscous oil with a $M_n$ of 820 D. The polycyclomethylsilazane (PCMS) produced a 57 wt % ceramic yield after pyrolysis under nitrogen. $^1H$ NMR ($CDCl_3$): 4.79, 4.68, 4.41 (m, 0.71 H, SiH), 0.89 (m, 0.56 H, NH), 0.19 (bs, 3 H, $SiCH_3$).

EXAMPLE 7

90° C. Polymerization of CMS (1/10 amount catalyst): 5.0 g CMS (from Example 2) and 1.0 mg (0.0015 mmoles) $Ru_3(CO)_{12}$ were combined under nitrogen in a quartz reactor. The reaction was heated at 90° C. and magnetically stirred. After 30 hours a very viscous oil is formed $^1H$ NMR ($CDCl_3$): 4.65, 4.40 (m, 0.69 H, SiH), 0.86 (m, 0.56 H, NH), 0.16 (m, 3 H, $SiCH_3$). This polycyclomethylsilazane (PCMS) produced a 63 wt % ceramic yield after pyrolysis under nitrogen. The ceramic yield after pyrolysis under $NH_3$ (to 850° C.) was 68 wt %. The $M_n$ was 1900 D.

The identical reaction carried out in the presence of $[Et_3SiRu(CO)_4]_2$ as catalyst gave a very viscous polymer with an $M_n$ of 1650 D.

EXAMPLE 8

Polymerization of CMS with $NH_3$ (90°): 5.0 g CMS (from Example 1) and 10.0 mg (0.0156 mmoles) $Ru_3(CO)_{12}$ were dissolved in 5.0 g THF and the solution was placed in a stainless steel pressure reactor under nitrogen Two equivalents of ammonia (130 psi) were added and the reaction was heated at 90° C. with magnetic stirring. After 2.5 hours, the pressure was released The solvent was removed from the reaction under vacuum producing a sticky, pale yellow wax. This material had a melting point at 10° C. and a $M_n$ of 1760 D. Elemental Analysis: %C 22.13, %H 7.38, %N 24.37, %Si 45.71. The material produced an 80 wt % ceramic yield after pyrolysis under nitrogen at 850° C. and 85 wt % under $NH_3$.

Elemental Analysis (of pyrolysis product): %C 14.44, %H 0 58, %N 25.74, %Si 52.67. $^1H$ NMR ($CDCl_3$): 4.80, 4.70, 4.42 (m, 0.62 H, SiH), 0.88 (m, 0.73 H, NH), 0.21 (bs, 3.0 H, $SiCH_3$).

EXAMPLE 9

Polymerization of CMS with $NH_3$ (60°): 5.0 g CMS (from Example 2) and 10.0 mg (0.0156 mmoles) $Ru_3(CO)_{12}$ were dissolved in 5.0 g THF and the solution was placed in a stainless steel pressure reactor under nitrogen. Two equivalents of ammonia (130 psi) were added and the reaction was heated at 60° C. and magnetically stirred. After 5 hours, the pressure had increased to 260 psi. The pressure was released and more $NH_3$ (130 psi) was added. After 5 more hours, an additional pressure of 70 psi had accumulated. As the solvent was removed from the reaction under vacuum a waxy solid is obtained by scraping. This solid had a melting point at 45°–55° C. and a molecular weight of 2210 D. $^1H$ NMR ($CDCl_3$): 4.77 (m, 0.34 H, SiH), 0.89 (m, 0.97 H, NH), 0.18 (m, 3 H, $SiCH_3$). The solid produced a 79 wt % ceramic yield after pyrolysis under nitrogen. Elemental Analysis (of pyrolysis product): %C 10.56, %H 0.45, %N 27.73, %Si 52.40.

EXAMPLE 10

"Curing" of APCMS (50° C.): Some of the product from Example 9 was dissolved in an equivalent weight of THF and stirred at 50° C. for 12 hours under nitrogen. The product after solvent removal was a solid with a softening point at 45°–55° C. and a melting point at 80°–90° C. The molecular weight had increased to 2400 D.

EXAMPLE 11

Increased Polymerization of APCMS (15 hours): A reaction mixture of amino-polymethylcyclosilazane (APCMS) was synthesized as in Example 9. (After 10 hours, the $M_n$ was 1930 D). The product, a sticky, soluble wax, was reacted with 130 psi of $NH_3$ at 60° C. After 5 more hours (15 hours total), only 110 psi had been generated. The solvent was then removed under vacuum, leaving a soft rubber. The ceramic yield of the rubber was 80 wt %.

EXAMPLE 12

"Curing" of APCMS at 60° C.: Some of the product from Example 11 after 10 hours of reaction was dissolved in an equivalent weight of THF and stirred at 60° C. for 4 hours under nitrogen. The product after solvent removal was a solid with a softening point at 50°–60° C. and a melting point at approx. 80° C. The molecular weight had increased to 2300 D.

EXAMPLE 13

Polymerization of CMS with $MeNH_2$ (60°): To 5.0 g THF in a stainless steel pressure reactor was added 5.0 g CMS (from Example 1) and 10.0 mg (0.0156 mmoles) $Ru_3(CO)_{12}$ under nitrogen. Two equivalents of $MeNH_2$ (130 psi) were added in portions and the reaction was heated at 60° C. with stirring for 5 hours. The pressure at this time had increased to 250 psi. The atmosphere above the reaction was released The solvent was removed from the reaction under vacuum to give a viscous, pale yellow oil. $^1H$ NMR ($CDCl_3$): 4.80, 4.66, 4.42 (m, 0.61 H, SiH), 2.48 (bs, 0.63 H, $NCH_3$), 0.80 (m, 0.78 H, NH), 0.17 (bs, 3.0 H, $SiCH_3$).

EXAMPLE 14

Polymerization of CMS with $MeNH_2$ (60° C.): To 5.0 g THF in a stainless steel pressure reactor was added 5.0 g CMS (from Example 2) and 10.0 mg (0.0156 mmoles) $Ru_3(CO)_{12}$ under nitrogen. Two equivalents of $MeNH_2$ (130 psi) were added in portions and the reaction was heated at 60° C. with stirring for 5 hours. The pressure at this time had increased to 180 psi. The atmosphere above the reaction was released and another 130 psi of $MeNH_2$ was added. After 5 more hours (10 hours total), only 50 psi of additional pressure had developed The solvent was removed from the reaction under vacuum to give a very viscous, pale yellow oil. The molecular weight ($M_n$) of this oil was 830 D. $^1H$ NMR ($CDCl_3$): 4.69 (m, 0.36 H, SiH), 2.46 (bs, 0.47 H, $NCH_3$), 0.65 (m, 0.96 H, NH), 0.16 (m, 3 H, $SiCH_3$). Elemental Analysis:

%C 23.40, %H 7.25, %N 23.17, %Si 33.42. The polymer was pyrolyzed under nitrogen to give a ceramic yield of 67%. Elemental Analysis (of pyrolysis products): %C 13.76, %H 0.51, %N 26.81, %Si 49.90.

EXAMPLE 15

Polymerization of CMS with MeNH? : 5.0 g CMS (from Example 3), 10.0 mg (0.0156 mmoles) $Ru_3(CO)_{12}$, and 5.0 g THF were added to a stainless steel pressure reactor under nitrogen. 2 equivalents of $MeNH_2$ (140 psi) were added in portions and the reaction was heated at 60° C. with stirring. After 2.5 hours, the pressure reached a maximum at 280 psi. After 3 hours, the solvent was removed from the reaction to give a very viscous oil which had a $M_n$ of 1394 D. $^1H$ NMR ($CDCl_3$): 4.81, 4.64 (m, 0.48 H, SiH), 2.44 (bs, 0.20 H, $NCH_3$), 0.80 (m, 0.69 H, NH), 0.14 (m, 3 H, $SiCH_3$).

EXAMPLE 16

"Curing" of MAPCMS at 60° C.: The oil produced in Example 15 was diluted with 1.5 g THF and reheated to 60° C. for 6 hours. The product was now almost a gel after solvent removal. This polymer was pyrolyzed under nitrogen to give a ceramic yield of 67 wt %. $^1H$ NMR ($CDCl_3$): 4.70 (m, 0.42 H, SiH), 2.46 (bs, 0.18 H, $NCH_3$), 0.83 (m, 0.59 H, NH), 0.14 (m, 3 H, $SiCH_3$).

EXAMPLE 17

Polymerization of CMS with $PdCl_2(C_6H_5CN)_2$ under $NH_3$ (60°): 5.0 g CMS (from Example 2), 6.0 mg (0.0156 mmoles) $PdCl_2(C_6H_5CN)_2$, and 5.0 g THF were added to a stainless steel pressure reactor under nitrogen. 130 psi of ammonia were added and the reaction was heated at 60° C. magnetically. After 5 hours, the pressure had increased by 60 psi. The pressure was released and 130 psi of $NH_3$ was added. After 5 more hours, only 30 psi pressure had accumulated. A slightly viscous black oil was obtained after removing the solvent from the reaction. This oil had a molecular weight of 976 D. $^1H$ NMR ($CDCl_3$): 4.83, 4.65, 4.40 (m, 0.74 H, SiH), 0.83 (m, 0.88 H, NH), 0.16 (m, 3 H, $SiCH_3$). Elemental Analysis: %C 21.86, %H 7.68, %N 5.01, %Si 42.39.

EXAMPLE 18

Polymerization of CMS in the presence of (hexyl)-$SiH_3$ at 60° C.: 10.0 mg (0.0156 mmoles) $Ru_3(CO)_{12}$ were added to 5.0 g CMS (from Example 4) and 2.0 g (hexyl)$SiH_3$ (17.2 mmoles). The reaction was stirred for 50 hours at 60°–90° C. Solvent removal after this time yielded only a slightly viscous green liquid. $^1H$ NMR ($CDCl_3$): 4.67, 4.36 (m, 0.94 H, SiH), 3.46 (m, 0.12 H, $SiH_x$), 1.28 (m, 0.97 H, $CH_2$), 0.86 (m, 0.36 H, $CH_3$), 0.22 (m, 0.24 H, $SiCH_2$), 0.18 (m, 3.0 H, $SiCH_3$). The $m_n$ of the polymer was 1450 D.

EXAMPLE 19

Precursor Formation: Into a flame-dried three-neck flask equipped with an overhead mechanical stirrer and an $N_2$ inlet was placed 500 ml anhydrous ether. This was cooled to $<-70°$ C. in a dry ice/acetone bath. Dichlorosilane (150 g; 1.5 moles) was then condensed into the flask. An excess of about 198 g (4.5 moles) monoethylamine was then added over a two-hour period. The reaction mixture was stirred for an additional four hours, and the flask was then allowed to warm slowly overnight to room temperature. The contents were diluted with 500 ml ether and filtered to remove monoethylamine hydrochloride salt.

The solids were then placed in a 2 l Erlenmeyer flask and stirred for 10 minutes in 500 ml boiling THF. The mixture was filtered hot. The extraction was repeated and the solids were rinsed with an additional 500 ml hot THF. 89.0 g of products were obtained after solvent removal (81% yield with $M_n$=490 D). Fractionation by high vacuum distillation (150°/300μ) gives 60% of volatile products having $M_n$ of 307 D and 40% residue with $M_n$=420 D.

EXAMPLE 20

Precursor Polymerization with $NH_3$ (90° C.): 5.0 g of the precursor $[EtN-SiH_2]_n$ prepared in Example 19 and 10.0 g (0.0156 mmoles) $Ru_3(CO)_{12}$ were placed in a stainless steel pressure reactor under nitrogen. Two equivalents of ammonia (160 psi) were added and the reaction mixture was heated at 90° C. with magnetic stirring. After 6 hours, the pressure was released The product, a very viscous liquid, was divided prior to pyrolysis in order to pyrolyze both under nitrogen and under ammonia. The ceramic yields obtained were 84 wt % ($N_2$) and 86 wt % ($NH_3$). Elemental analysis (in mole ratios) was as follows:

|  | C | H | N | Si | O |
|---|---|---|---|---|---|
| Polymer before pyrolysis | 1.42 | 5.69 | 1.33 | 1.00 | 0.11 |
| Polymer after pyrolysis under $NH_3$ | 0.48 | 0.58 | 1.05 | 1.00 | 0.05 |
| Polymer after pyrolysis under $NH_3$ | 0.24 | 0.55 | 1.44 | 1.00 | 0.03 |

EXAMPLE 21

Polysilazane Coatings: Coatings of the polysilazane precursor of Example 5 were prepared by dipping soda lime rods, 3 mm in diameter, into polysilazane solutions ($M_n$ of about 2000 D) in THF having concentrations of 2.5 wt. %, 5 wt. % and 10 wt. %. The samples were cured under a slow pyrolysis regime (heating rate of about 100° C./hr) to a final temperature of 590° C. The cured coatings were transparent and smooth. The thickness of the cured coating was measured by SEM and found to be in the range of 0.1 and 0.5 microns for the 2.5 wt. % and 5 wt. % solutions and in the range of 1.0 and 4.0 microns for the 10 wt. % solution.

EXAMPLE 22

Figure 1:
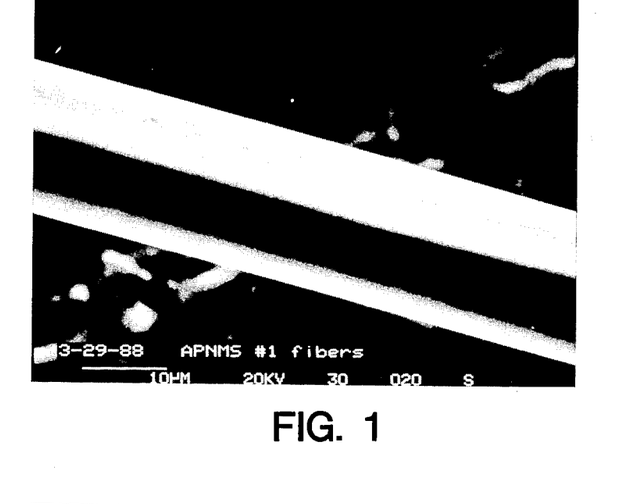
FIGS. 1 and 2 are SEM photographs of the polysilazane fiber prepared as described in Example 22.
Figure 2:
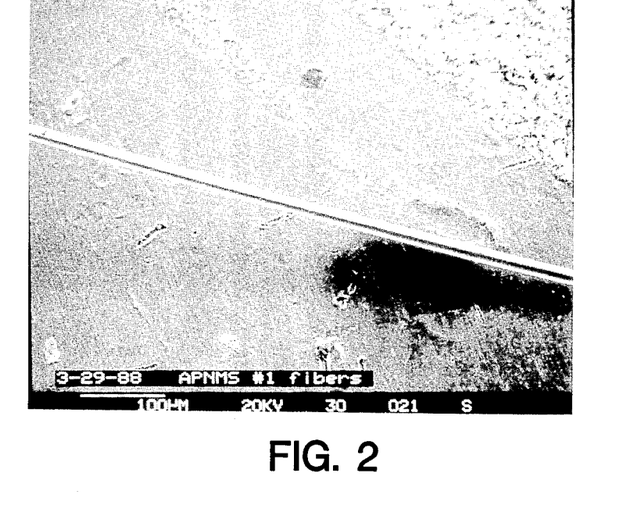

Fiber Preparation Fibers of about 4" to 24" were formed from the polymer of Example 8, a soft wax, at room temperature These fibers were cured under ammonia for approximately 3 hours, again at room temperature. After curing, the fibers were heated under ammonia, first to 250° C. at a heating rate of 60°/hour, and then to 850° C. at a heating rate of 300°/hour. The ceramic fibers obtained after pyrolysis had diameters on the order of 4 to 50 microns, and maintained their shape without any flaws or breakage FIGS. 1 and 2 are SEM photographs of a fiber prepared according to this procedure.

We claim:

1. A method of making a polysilazane having n recurring units of the structures (I) or (II) or both (I)

(II)

where m is 0 or an integer, n is an integer greater than 1, the R substituents may be the same or different and are selected from the group consisting of hydrogen, lower alkyl, lower alkenyl, silyl, aryl, and amino, unsubstituted or substituted with 1 or 2 lower alkyl groups, X is —NR'— or —NR'—Y—NR'— where Y is an optional linking group which, if present, is lower alkyl or silyl, and the R' and R" may be the same or different and are independently selected from the group consisting of hydrogen, lower alkyl, lower alkenyl, silyl and aryl, wherein the method comprises (a) providing a silazane precursor having one or more units of the formula wherein the precursor contains either (i) at least one N—H bond and at least one Si—H bond, or (ii) at least two Si—H bonds, or both; and (b) reacting the precursor in the presence of a transition metal catalyst.

2. The method of claim 1, wherein said reacting is carried out in a solvent for the silazane precursor.

3. The method of claim 1, wherein said reacting is carried out in the presence of gaseous ammonia.

4. The method of claim 1, wherein said reacting is carried out in the presence of a co-reactant given by the structure NH₂ where is hydrogen, lower alkyl, silyl optionally substituted with one or more alkyl groups, or —(CH₂)$_x$NH₂ where x is an integer in the range of 0 to 20 inclusive.

5. The method of claim 1, wherein the reaction of the precursor is carried out at a temperature in the range of about 0° C. to 150° C.

6. The method of claim 5, wherein the reaction of the precursor is carried out at a temperature in the range of about 20° C. to 90° C.

7. The method of claim 1, wherein the transition metal catalyst is a homogeneous catalyst, a heterogeneous catalyst, or a mixture or mixtures thereof.

8. The method of claim 6, wherein the transition metal catalyst is a ruthenium catalyst.

9. The method of claim 1, wherein said reacting is carried out in the presence of a co-reactant given by the structure R'''₂SiH₂ and R''' is hydrogen or lower alkyl.

10. The method of claim 1, wherein the precursor includes one or more silazane bridge groups given by the structure

11. The method of claim 1, wherein the precursor includes cyclomers bridged by one or more amine groups.

12. The method of claim 1, wherein the precursor includes cyclomers bridged by one or more silyl groups.

13. The method of claim 1, wherein the precursor is CMS, and the reaction is carried out in ammonia gas using a ruthenium catalyst.

14. The method of claim 1, wherein the precursor is CMS, and the reaction is carried out in monomethylamine gas using a ruthenium catalyst

15. Polysilazanes consisting essentially of n recurring units of the structures (I) or (II) or both (I)

(II)

wherein m is 0 or an integer, n is an integer greater than 1, the R substituents may be the same or different and are selected from the group consisting of hydrogen, lower alkyl, lower alkenyl, silyl, aryl, and amino, unsubstituted or substituted with 1 or 2 lower alkyl groups, X is —NR'— or —NR'—Y—NR'— where Y is an optional linking group which, if present, is lower alkyl or silyl, and the R' and R" may be the same or different and are independently selected from the group consisting of hydrogen, lower alkyl, lower alkenyl, silyl and aryl.

16. Polysilazanes consisting essentially of n recurring units of the structure (I)

(I)

wherein m is 0 or an integer, n is an integer greater than 1, the R substituents may be the same or different and are selected from the group consisting of hydrogen, lower alkyl, lower alkenyl, silyl, aryl, and amino, unsubstituted or substituted with 1 or 2 lower alkyl groups, X is —NR'—or —NR'—Y—NR'—where Y is an optional linking group which, if present, is lower alkyl or silyl, and the R' and R" may be the same or different and are independently selected from the group consisting of hydrogen, lower alkyl, lower alkenyl, silyl and aryl.

17. Polysilazanes consisting essentially of n recurring units of the structure (II)

wherein m is 0 or an integer, n is an integer greater than 1, the R substituents may be the same or different and are selected from the group consisting of hydrogen, lower alkyl, lower alkenyl, silyl, aryl, and amino, unsubstituted or substituted with 1 or 2 lower alkyl groups, and the R, substituents are independently selected from the group consisting of hydrogen, lower alkyl, lower alkenyl, silyl and aryl.

18. Ceramic fibers spun from the polysilazanes of claim 15.

19. Ceramic fibers spun from the polysilazanes of claim 16.

20. Ceramic fibers spun from the polysilazanes of claim 17.

* * * * *

UNITED STATES PATENT AND TRADEMARK OFFICE
CERTIFICATE OF CORRECTION

PATENT NO. : 4,952,715
DATED : August 28, 1990
INVENTOR(S) : Yigal D. Blum, et. al.

It is certified that error appears in the above-indentified patent and that said Letters Patent is hereby corrected as shown below:

Column 19, line 7, replace "MeNH?" with --MeNH$_2$--.

Column 21, claim 4, line 3, replace "NH$_2$ where is" with --$\gamma$NH$_2$ where $\gamma$ is--.

Column 21, claim 5, line 1, replace "!" with --1--.

Signed and Sealed this

Twenty-eighth Day of September, 1993

Attest:

BRUCE LEHMAN

*Attesting Officer*  *Commissioner of Patents and Trademarks*